United States Patent [19]
Saito et al.

[11] Patent Number: 4,910,144
[45] Date of Patent: Mar. 20, 1990

[54] YEAST STRAIN WITH HIGH POWER TO PRODUCE ALCOHOL BY FERMENTATION

[75] Inventors: Kazuo Saito; Hitoshi Shimoi; Shunichi Sato; Makoto Tadenuma; Kiyoshi Yoshizawa; Kazuhito Moriya; Chikashi Izumi, all of Tokyo, Japan

[73] Assignees: Tax Administration Agency, Ministry of Finance; Hokkaido Sugar Co., Ltd., both of Tokyo, Japan

[21] Appl. No.: 139,786

[22] Filed: Dec. 30, 1987

[30] Foreign Application Priority Data

Jul. 27, 1987 [JP] Japan .............................. 62-185565

[51] Int. Cl.$^4$ ........................ C12N 1/16; C12R 1/86; C12P 7/06
[52] U.S. Cl. .................................. 435/256; 435/161; 435/165; 435/172.1; 435/172.2; 435/255; 435/942
[58] Field of Search .................... 435/942, 172.1, 255, 435/256, 172.2, 161, 165

[56] References Cited

U.S. PATENT DOCUMENTS

| | | | |
|---|---|---|---|
| 4,396,632 | 8/1983 | Clement et al. | 435/172.1 |
| 4,560,659 | 12/1985 | Asturias | 435/942 |
| 4,562,154 | 12/1985 | Watanabe et al. | 435/942 |
| 4,643,901 | 2/1987 | Jacobson et al. | 435/942 |

Primary Examiner—Herbert J. Lilling
Attorney, Agent, or Firm—Oblon, Spivak, McClelland, Maier & Neustadt

[57] ABSTRACT

A yeast strain with high power to produce alcohol by fermentation is produced by a method comprising directly conjugating the haploid of the strain No. 909-1 with each tetrad of the ascospores of the strain No. 180 by spore-to-cell mating, acclimating the resultant zygote in the medium of waste after alcohol fermentation, and acclimating the surviving cells of the zygote in the medium of the beet molasses containing 2-deoxyglucose. The yeast strain produced is designated as Strain M-9 (FERM BP 1481) of genus *Saccharomyces cerevisiae*. Alcohol is produced by culturing the Strain M-9 in a medium of beet molasses.

1 Claim, 2 Drawing Sheets

YEAST STRAIN WITH HIGH POWER TO PRODUCE ALCOHOL BY FERMENTATION

BACKGROUND OF THE INVENTION

Field of the Invention

This invention relates to a yeast strain exhibiting high power to produce alcohol by fermentation of beet molasses as raw material, for example, and to a method for production of fermentation alcohol by the use of the yeast strain.

Prior Art Statement

Cane molasses has found utility in numerous applications such as, for example, the provision of raw material for production of alcohol by fermentation and the culture of bakers' yeast.

In contrast, beet molasses which remains after separation of sucrose from beet is usable only as an additive to animal feed and has virtually no other utility.

One conceivable way of expanding the uses for beet molasses is to use it for the production of spirits by the fermenting it into alcohol. The inventors screened yeasts in search of yeast strains which are suitable for such fermentation. As a result, they have found that the two yeast strains, i.e. a flocculent yeast strain NRIB No. 180 (serial number assigned by National Research Institute of Brewing, Tax Administration Agency of Japan) and a killer yeast strain No. 909-1 (serial number assigned by Tax Administration Agency of Japan), belonging to genus *Saccharomyces cerevisiae* exhibit a highly desirable fermentability to produce alcohol from beet molasses by fermentation.

In commercial production of alcohol by fermentation using a yeast strain, since the process of fermentation is usually carried out in an open condition, there is an undeniable possibility that some wild yeast will find its way into the fermentation tank and do harm. The yeast used for the fermentation, therefore, is required to possess killer phenotype against invading other harmful wild yeasts. Further, since the yeast is used repeatedly, it is required to possess also a flocculent property to be effectively separated from the fermentation mash. The two yeast strains mentioned above have only one or the other of the two properties, namely killer phenotype or the flocculent property. Neither of these yeast strains, therefore, is capable of efficiently effecting production of alcohol on a commercial scale.

OBJECT AND SUMMARY OF THE INVENTION

An object of this invention is to provide a yeast strain which exhibits the killer phenotype and the flocculent property in combination and which, in alcohol production using beet molasses, effects the fermentation with high efficiency and produces alcohol in high concentration.

Another object of this invention is to provide a method which permits the alcohol production using the aforementioned yeast strain to be carried out efficiently on a commercial scale.

To accomplish the objects described above, this invention obtains with high repeatability a yeast strain possessing the killer phenotype and the flocculent property and effecting the alcohol production in high yield by a procedure which comprises directly conjugating two yeast strains belonging to *Saccharomyces cerevisiae*, one capable of exhibiting highly desirable alcohol production power with respect to beet molasses and, at the same time, possessing a flocculent property and the other capable of exhibiting a killer phenotype, culturing the conjugated strain in the distilled wasted water after a fermentation process for alcohol production, and subjecting the resultant acclimated strain to further catabolite derepressed mutation beet molasses containing nonmetabolizable glucose analogue 2-deoxyglucose.

The yeast strain described above possesses the killer phenotype and excels in the flocculent property. When production of alcohol using this yeast strain is carried out on a commercial scale, the fermentation can be carried out in an open reaction tank by using the beet molasses in an unboiled state because the yeast strain exhibits the killer phenotype against the invading other harmful wild yeast. Further, since the yeast strain excels in the flocculent property, it can be easily separated from the fermentation broth and put to use repeatedly. Thus, this yeast strain enables the alcohol production to be carried out efficiently on a commercial scale by a batchwise or continuous process without requiring any special means for separation.

The above and other objects and features of the invention will become more apparent from the following detailed description with reference to the accompanying drawings.

DETAILED DESCRIPTION OF THE PREFERRED EMBODIMENT

Figure 1:
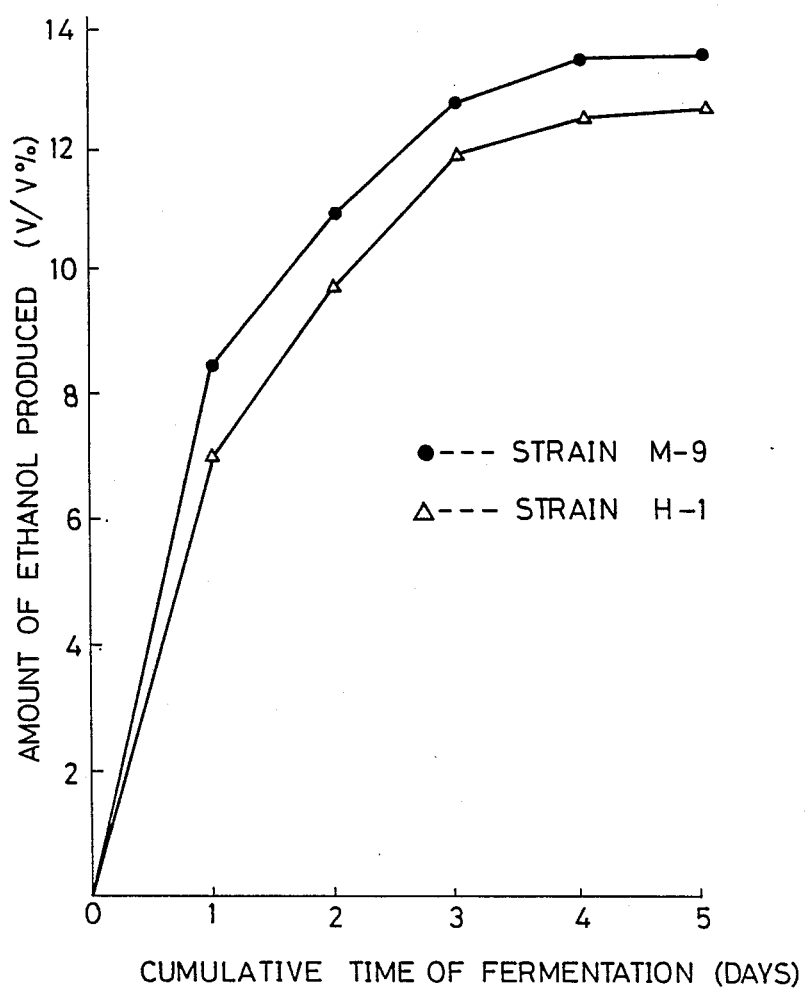
FIG. 1 is a graph showing the time course change in the production of ethanol according to the present invention.

The inventors conducted a search for a yeast strain which possesses both the killer phenotype and the flocculent property and produces alcohol fermentation effectively. As a result, they succeeded in obtaining a yeast strain designated as strain No. H-1 of genus *Saccharomyces cerevisiae* and excelling in the flocculent property and the killer phenotype, by conjugating strain No. 180 rich in the flocculent property with strain No. 909-1 rich in the killer phenotype.

To be specific, the strain No. 909-1 (diploid) is heterothallic and has killer phenotype and the strain No. 180 (diploid) of genus *Saccharomyces cerevisiae* is homothallic and flocculent. First, the strain No. 909-1 was caused to form spores in the cell thereof. Then, the cells were treated with a cell wall lytic enzyme and the spores were dispersed on a plurality of plate media (agar medium containing yeast extract, peptone and dextrose) for growth of colonies. The strains from the colonies grown on the agar media were severally used to effect production of alcohol using beet molasses. The haploid (mating type a) was screened out of the strain from the colonies on the media which exhibited a high survival ratio and alcohol productivity at the end of the fermentation.

Separately, the strain No. 180 (homothallic diploid) of genus *Saccharomyces cerevisiae* which is a flocculent yeast was likewise caused to form spores on the asci thereof. With every four spores of the strain No. 909-1 consequently formed, the direct conjugation was carried out with the haploid of the strain No. 180 by spore-to-cell mating. This conjugation was established in a probability of about ½. With the consequent formation of a zygote kept confirmed, the zygote was cultured successively in a number of plate media to obtain a plurality of colonies. Then, the strains from these colonies were severally used to effect production of alcohol. From the fermentation broths, the particular strain which had given yeast cells in a high survival ratio after the fermentation is screened out from the colonies on the plate media.

The strain screened out in the procedure described above was designated as strain H-1 and submitted on July 31, 1986 with the Fermentation Research Institute, Tsukuba, Japan, and deposited under the number FERM P-8885.

The taxonomic tests ("The Yeast", a taxonomic study, 3rd ed., edited by N. J. W. Kreger van Rij) performed on the H-1 strain produce the following results.
Spore formation: Positive
Fermentation of sugars: Positive invariably with glucose, galactose, sucrose, maltose, and raffinose
Assimilation of carbon sources: Positive invariably with glucose, galactose, sucrose, maltose, trehalose, raffinose, and α-methyl-D-glucoside and weakly positive with melezitose and DL-lactic acid.
Assimilation of nitrates: Negative
Vitamin demand: Negative
Growth at 37° C.: Positive
Growth in 10% NaCl medium: Positive Based on these results, the strain has been identified as genus *Saccharomyces cerevisiae*.

While the strain H-1 has killer phenotype and flocculent property, it was observed to be substantially destroyed when cultured in the distilled wasted water from the fermentation process for production of alcohol using beet molasses.

This phenomenon is possible due to the fact that the waste contains certain growth inhibiting materials. It is accordingly concluded that when a variant resistant to the growth inhibiting materials is derived from the strain H-1, it will exhibit a high power to produce alcohol by fermentation.

The strain H-1 was cultured in the distilled wasted water after ethanol fermentation using beet molasses. Viable yeasts after incubation were repeatedly inoculated in the beet molasses. Then, the viable yeast cells after ten times cultivation were inoculated to a plurality of agar media containing the distilled wasted water and cultured therein for growth of colonies. The colonies grown on the plate media were used to effect production of alcohol with beet molasses. From the resultant fermentation broths, the strains which had produced yeast cells in a high survival ratio after fermentation were screened out.

Subsequently, the screened strains were successively cultured in several cycles using beet molasses containing 2-deoxyglucose (2DOG). The strain from the last cycle of the culture was inoculated to a plurality of 2DOG-containing beet molasses agar media and cultured for growth of colonies. In consequence of this treatment, there were obtained colonies which were derepressed of catabolite repression. The strains from the colonies were used to effect production of alcohol from beet molasses. The particular strain which had produced yeast cells in a high survival ratio after fermentation was screened out. The strain thus screened out by the procedure described above was designated as strain M-9 and deposited on June 6, 1987, with the Fermentation Research Institute of Tsukuba, Japan, under the number FERM P-9401. On Sept. 24, 1987, application for alteration of the status of deposition was filed in compliance with the Budapest Convention, and the strain was assigned the deposition number FERM BP-1481.

When the same taxonomic tests as performed on the aforementioned strain H-1 were carried out on this strain M-9, the results were the same as those obtained of the strain H-1. The description of the characteristics of the strain M-9, therefore, will be omitted.

Based on these test results, the strain has been identified as a variant of the strain H-pb 1 of genus *Saccharomyces cerevisiae*.

The strain M-9 exhibits a highly desirable power to produce alcohol by fermentation with respect to such substrates as beet molasses and, at the same time, possesses outstanding qualities with respect to flocculent property, killer phenotype, fitness for continuous use through successive cycles of fermentation, and repeatability of fermentation power.

As examples of the raw material for the production of alcohol by the use of the strain mentioned above, there can cited in addition to beet molasses, cane molasses, sweet potato, potato, casaba, rice, agricultural waste, and hydrolyzates thereof. Since the strain of the present invention possesses the killer phenotype, the step for sterilization can be simplified as by using the raw material in an unboiled state. The amount of the strain to be used for alcohol production varies with the kind of the raw material adopted. In the case of batchwise fermentation using beet molasses, for example, cells concentration of the strain sufficient for fermentation is in the range of $10^5$ to $10^8$ cells/ml. In the case of continuous fermentation, the amount of the strain sufficient for the fermentation is in the range of $10^5$ to $10^9$ cells/ml as cell concentration in the tank.

The fermentation is generally carried out under the conditions of pH 4 to 6 and 25° to 37° C. of temperature (preferably in the neighborhood of 30° C.).

The fermentation can be carried out batchwise in a stirring tank or continuously. The batchwise fermentation is suitable mainly for the production of spirits and the continuous fermentation mainly for the production of alcohol for fuel.

Further, since the strain M-9 of the present invention displays a distinct ability to flocculate and sediment in a fermentation mash, it permits the continuous fermentation to be carried out at a high charging concentration without requiring the sedimentation tank to be provided with any special means for separation. Thus, the strain has an advantage that the system for the continuous fermentation can be designed in a compact construction.

Now, the present invention will be described more specifically below with reference to examples. It should be noted, however, that this invention is not limited to the following examples.

EXAMPLE 1

In a medium containing 1% potassium acetate, 0.2% yeast extract, 0.2% glucose, and 2% agar, the strain 909-1 of genus *Saccharomyces cerevisiae* was cultured to form ascospores. The ascospores consequently formed were exposed and dispersed by using a cell wall lytic enzyme (Zymolyase 100T) and each tetrad of the ascospores were then dissected with a micromanipulator. The respective spores were inoculated on an agar medium containing 1% yeast extract, 2% peptone, 2% glucose, and 2% agar and cultured. The 32 colonies grown in the medium were severally subjected to a screening treatment under the following conditions.

The beet molasses containing 10% of total sugar was used as a culture medium. This culture medium was supplemented with 700 ppm $KH_2PO_4$, adjusted to pH 5.0 and sterilized in an autoclave. To the media treated as described above, the strains taken each by one loop from the aforementioned 32 haploid colonies were inoculated and shaken cultured at 30° C. for two days. As a result, 32 yeast suspensions were obtained.

Then, 32 culture media of the beet molasses having total sugar content adjusted to 24% were prepared, adjusted to pH 5.0, and sterilized in an autoclave. Then, to the sterilized media each in a fixed volume of 250 ml, the aforementioned cultured yeast suspensions were added in amounts calculated to give a fixed concentration of $4 \times 10^7$ cells/ml. The resultant culture mixtures were subjected to five days' fermentation at 30° C. After fermentation, the particular strain which produced a high alcohol content in the culture broth compared to parental strain was screened out.

Separately, in a spore forming medium of the same composition as used in the preceding treatment, the strain 180 of genus *Saccharomyces cerevisiae* was cultured. The screened strain mentioned above was directly conjugated with every four ascospores formed on the medium by the spore-to-cell mating. The conjugated strain was cultured on a plate medium at a temperature of about 30° C. and observed under a microscope for confirmation of the formation of zygotes along the course of time. The conjugated strain which was found to form zygote was selected as a mating strain.

The selected 32 strains were shaken cultured at 30° C. for two days on a sterilized medium of beet molasses having total sugar content adjusted to 10%, containing 700 ppm $KH_2PO_4$ and adjusted to pH 5.0. Then, each of the cultured cells mentioned above was inoculated on one of 32 sterilized media of beet molasses having the total sugar content and pH value adjusted to 24% and 5.0 respectively and was fermented therein. The particular strain which produced alcohol in the highest concentration in the culture broth compared to parental strains was screened out. This strain was the strain H-1 aforementioned and the ratio in which a strain possessing the same degree of alcohol production power would be produced by the procedure mentioned above was more than 70%.

Subsequently, the strain H-1 thus obtained was inoculated on a distilled wasted water medium containing 50,000 ppm of TOC (total organic carbon), and subjected to two days' shaken culture at 30° C. The viable cells after the cultivation were repeatedly cultured in the same distilled wasted water medium under the same conditions as described above. This procedure was repeated 10 times. The viable cells after the 10th cycle of culture were inoculated on a distilled wasted water medium containing 2% agar and cultured therein for two days at 30° C. The 32 strains were taken from the colonies grown consequently on the medium. A total of 32 media of beet molasses containing 10% of total sugar and 700 ppm $KH_2PO_4$ were adjusted to pH 5.0 and sterilized in an autoclave. To the 32 media so treated, the strains were inoculated each in one loop to be subjected therein to two days' shaken culture at 30° C. As a result, there were obtained yeast suspensions (culture broth).

A culture medium of beet molasses containing 24% of total sugar was prepared, adjusted to pH 5.0, and sterilized in an autoclave. The sterilized culture medium was divided into 32 media each having a volume of 250-ml. In each of the divided media, the aforementioned yeast suspensions were added in amounts calculated to give a fixed concentration of $4.0 \times 10^7$ cells/ml and subjected to alcohol fermentation. The particular strain which produced yeast cells in a high ethanol productivity survival ratio compared with parental strains after the fermentation was screened out.

A culture medium of beet molasses (containing 10% of total sugar and 700 ppm $KH_2PO_4$, pH 5.0) was prepared and 2-deoxyglucose (2DOG) was added thereto in a concentration of 150 ppm. In the culture medium formed consequently, the aforementioned screened strain was cultured at 30° C. for two days. The cultured strain was inoculated and cultured on the 2DOG-containing beet molasses agar culture medium (agar content 2%). The colony formed on the medium was selected and inoculated to a new medium of the same composition. The procedure described above was repeated in a total of three cycles. The large single colonies grown on the 2DOG-containing agar medium were cultured on the aforementioned beet molasses culture medium at 30° C. for two days. Cells grown on the beet molasses medium were inoculated on 32 media of beet molasses containing 24% of total sugar and adjusted to pH 5.0 and were subjected to alcohol fermentation at 30° C. for five days. Only the strains which produced alcohol concentration exceeding 13.5% were screened out. Thus, the strains M-9 were obtained.

EXAMPLE 2

As a culture medium, there was used 250 ml of beet molasses having its total sugar content of 10%, and supplemented with 700 ppm $KH_2PO_4$, adjusted to pH 5.0 and sterilized in an autoclave. In the culture medium thus treated, one loop of the strain M-9 obtained in Example 1 was inoculated and subjected to two days' shaken culture at 30° C.

A 500 ml culture medium of beet molasses containing 24% of total sugar and 700 ppm $KH_2PO_4$ was adjusted to pH 5.0. This culture medium was placed in a fermentation jar having an inner volume of 1,000 ml and the aforementioned cultured strain M-9 was inoculated on the culture medium in a concentration of $1 \times 10^8$ cells/ml. Then, the contents of the jar were stirred (100 to 200 rpm) anaerobically at 30° C. for five days for ethanol production.

For comparison, ethanol production was carried out by following the procedure described above, except that the strain corresponding to strain H-1 obtained in Example 1, which is a parental strain of the strain M-9, was used instead. The results are shown in FIG. 1.

From the results, it is clearly noted that in the case of the strain H-1, the speed of ethanol fermentation was relatively high but leveled off at 12.8 V/V % on the fifth day of fermentation.

In contrast, in the case of the strain M-9, the initial speed of ethanol production exceeded that with the strain H-1, and, what is more, the ethanol production reached about 13.5 V/V % on the fourth day of fermentation. As a result, the final ethanol concentration surpassed 1 V/V % in a shorter span of time than the strain H-1. The numbers of viable cells in the fermentation solutions (cells/ml) on the fifth day of fermentation are shown in Table 1.

TABLE 1

| Strain H-1 | Strain M-9 (cells/ml) |
|---|---|
| $1 \times 10^7$ | $7 \times 10^7$ |

It is clear from the results that the number of cells of the strain M-9 was 7 times that of the strain H-1 even after completion of fermentation and that the number was close to the number of cells existing at the time of inoculation.

EXAMPLE 3

A 2% YM culture medium (a product of Difco Corp. marketed under tradename designation of "YM Broth") was sterilized in an autoclave. In the sterilized culture medium, one loop of culture from the slant stock of the strain M-9 obtained in Example 1 was inoculated and shaken cultured at 30° C. for two days.

Then, a culture medium of cane molasses containing 24% of total sugar, 0.1% $(NH_4)_2SO_4$ and 0.1% $KH_2PO_4$ was adjusted to pH 5.0 and sterilized in an autoclave. In 250 ml of the medium so·treated, the aforementioned culture yeast suspension was inoculated in an amount calculated for the strain M-9 to be contained therein in a concentration of $4.0 \times 10^7$ cells/ml and subjected to fermentation for ethanol production for four days.

The results were as shown in Table 2 below.

TABLE 2

| Time (days) | Amount of ethanol produced (V/V %) |
|---|---|
| 1 | 11.9 |
| 2 | 13.50 |
| 3 | 13.75 |
| 4 | 13.80 |

EXAMPLE 4

A 250 ml culture medium of beet molasses containing 10% of total sugar and 700 ppm $KH_2PO_4$ was adjusted to pH 5.0 and then sterilized in an autoclave. In the culture medium, one loop of the strain M-9 obtained in Example 1 was inoculated and shaken cultured at 30° C. for two days.

Then, in 250 ml of beet molasses adjusted to a total sugar content of 15% and pH 5.0, the cultured strain M-9 was inoculated in an amount computed to correspond to an initial cell number of $1 \times 10^8$ cells/ml and anaerobically stirred with a magnetic stirrer at a rate of about 100 rpm at 30° C. for two days, to effect fermentation. After completion of the fermentation, the fermentation solution was left standing at rest for 10 minutes. As a result, the cells were sedimented and compacted to less than 1/10 of the total volume of the fermentation solution. The supernatant which formed in the fermentation solution after completion of the production of ethanol was removed and the remaining fermentation solution was replenished with fresh beet molasses of the aforementioned concentration to make up for the volume lost by the removal. The fermentation solution thus prepared was subjected to fermentation under the same conditions. The procedure described above was repeated up to a total of five cycles. The amounts of ethanol produced and the numbers of viable cells formed severally in the five cycles were as shown respectively in FIG. 2 and Table 3.

TABLE 3

| Cycle of batchwise fermentation | Initial number of cells (per ml) | Final number of cells (per ml) |
|---|---|---|
| First | $1 \times 10^8$ | $9 \times 10^7$ |
| Second | $9 \times 10^7$ | $9 \times 10^7$ |
| Third | $9 \times 10^7$ | $9 \times 10^7$ |
| Fourth | $9 \times 10^7$ | $8 \times 10^7$ |
| Fifth | $8 \times 10^7$ | $7 \times 10^7$ |

Figure 2:
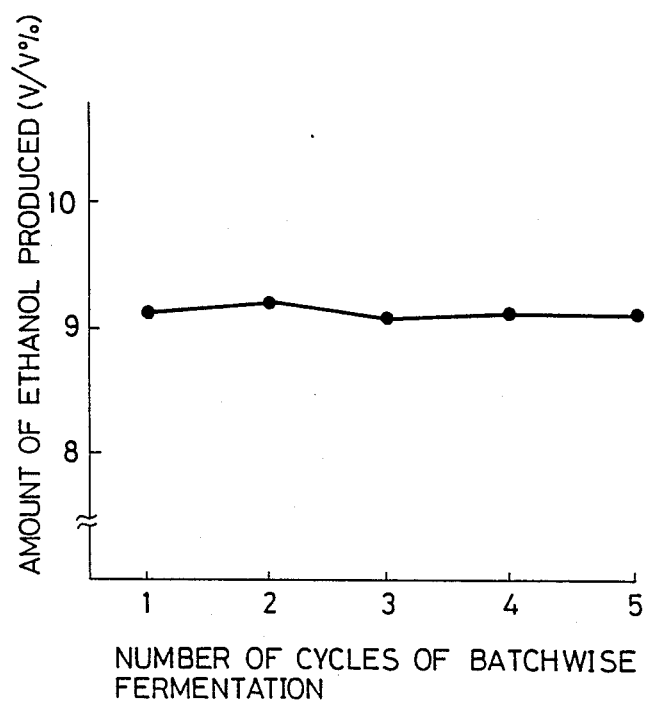
FIG. 2 is a graph showing the amounts of alcohol produced in each of five fermentation batches.

It is clearly noted from FIG. 2 that the production of alcohol by continued use of the strain was stable when the sugar concentration was 15%. It is also noted from the foregoing table that the number of viable yeast cells after fermentation was the same as that existing at the time of inoculation. After completion of the fermentation, the yeast cells were readily sedimented in a short span of time when the fermentation solution was merely left standing at rest, to give rise to a slurry of high density and form a clear fermentation solution as a result.

EXAMPLE 5

The strain M-9 of Example 1 and the strain 909-1 as a control were anaerobically cultured as stirred at 30° C. The fermentation solutions were sampled during the course of stirring and after one minute's standing at rest following the completion of stirring and the samples were tested for turbidity (O.D.: absorbance measured with a 10-mm cell at a wavelength of 660 nm) and the percentage of the volume of cells occupied in the fermentation solution. The results were as shown in Table 4.

TABLE 4

| | Turbidity (O.D.) | |
|---|---|---|
| Strain | During the course of stirring (O.D.) | After one minute's standing at rest (O.D.) |
| M-9 | 8.0 | 0.10 |
| 909-1 | 8.44 | 7.50 |

| | Percentage of volume of cells occupied in fermentation solution | |
|---|---|---|
| Strain | During the course of stirring (%) | After one minute's standing at rest (%) |
| M-9 | 100% | 5 (95% of supernatant) |
| 909-1 | 100% | 99 (1% of supernatant) |

It is clear from the results shown above that the fermentation solution of the strain 909-1 remained in its suspended state even after one minute's standing at rest following the completion of the stirring, whereas the fermentation solution of the strain M-9 underwent immediate flocculation and sedimentation after stirring was stopped and completed sedimentation and separation within one minute. In this case, the yeast cells were sedimented and compacted to less than 1/10 of the total volume of the fermentation solution. The supernatant was a clear solution containing few yeast cells.

Owing to the nature of the strain M-9 described above, the separation of the yeast cells after completion of the fermentation could be effected by simply allowing the fermentation solution to stand at rest without requiring use of any mechanical device such as a centrifugal separator or a plain separator. Thus, the separation of the yeast cells from the fermentation solution is attained in a matter of several minutes. Immediately, the supernatant can be forwarded to the step of distillation and the sedimented yeast cells can be recycled for reuse.

EXAMPLE 6

In a culture medium of beet molasses adjusted to a total sugar content 24% and pH 5.0, *Saccharomyces cerevisiae* Kyokai No. 701 (serial number assigned by the Society of Brewing, Japan) and the strain M-9 were inoculated in an amount of $5\times10^8$ cells/ml and in an amount of $5\times10^7$ cells/ml, respectively, and stirred at 30° C. for mixed culture for one day. At the end of the culture, the culture solution was tested for determining the number of viable cells of the strain M-9 and that of the strain Kyokai No. 701 by the use of a β-alanine agar medium (the Society of Brewing, Japan).

As a control, the strain Kyokai No. 701 and strain M-9 were separately inoculated and cultured under the same conditions and each of the culture solution was tested for determining the number of viable cells. The results were as shown in Table 5 below.

TABLE 5

| | Strain | Initial number of cells (per ml) | Final number of cells (per ml) |
| --- | --- | --- | --- |
| Mixed culture | M - 9 | $5 \times 10^7$ | $1 \times 10^8$ |
| | Kyokai 701 | $5 \times 10^8$ | $8 \times 10^4$ |
| Control (single culture) | Kyokai 701 | $5 \times 10^8$ | $8 \times 10^8$ |
| | M - 9 | $5 \times 10^7$ | $1 \times 10^8$ |

It is noted from the results shown above that the strain Kyokai No. 701 which existed in an amount 10 times that of the strain M-9 at the time of inoculation decreased to about 1/1,000 after one day's culture, indicating gradual extinction during the course of the culture. In contrast, the number of cells of the strain M-9 remained unchanged, indicating that the strain M-9 possessed a killer phenotype against other yeasts.

What is claimed is:

1. A high power yeast strain to produce alcohol from beet molasses by fermentation, designated as Strain M-9 (FERM BP 1481) of the genus *Saccharomyces cerevisiae*.

* * * * *